United States Patent
Mottram et al.

(10) Patent No.: US 6,270,462 B1
(45) Date of Patent: Aug. 7, 2001

(54) APPARATUS FOR ANIMAL HEALTH MONITORING (75) Inventors: Toby Trevor Fury Mottram, Royston; Helen Rebecca Whay, Thetford; Steven George Vass, Ampthill, all of (GB); Birte Lindstrom Nielsen, Foulum (DK)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/497,387

(22) Filed: Feb. 3, 2000

Related U.S. Application Data (63) Continuation of application No. PCT/GB98/02302, filed on Aug. 3, 1998.

(30) Foreign Application Priority Data

Aug. 4, 1997 (GB) .................................................. 9716425

(51) Int. Cl.⁷ ............................................................ A61B 5/08
(52) U.S. Cl. ............................. 600/529; 600/538; 600/543
(58) Field of Search ..................................... 600/529, 531, 600/532, 533, 534, 535, 536, 537, 538, 539, 540, 541, 542, 543; 119/417, 421, 418, 174, 712

(56) References Cited

U.S. PATENT DOCUMENTS

| 3,972,326 | * | 8/1976 | Brawn | 128/202.15 |
|---|---|---|---|---|
| 4,114,616 | * | 9/1978 | Brawn | 128/202.15 |
| 4,391,283 | * | 7/1983 | Sharpless et al. | 600/538 |
| 4,495,944 | * | 1/1985 | Brisson et al. | 600/538 |
| 4,830,022 | * | 5/1989 | Harshe et al. | 600/537 |
| 4,945,918 | | 8/1990 | Abernathy . | |
| 5,265,618 | | 11/1993 | Zimmerman . | |
| 6,129,680 | * | 10/2000 | Mottram | 600/532 |

FOREIGN PATENT DOCUMENTS

97/00444   1/1997  (WO) .

* cited by examiner

Primary Examiner—Eric F. Winakur
Assistant Examiner—Navin Natnithithadha
(74) Attorney, Agent, or Firm—Nixon & Vanderhye (57) ABSTRACT

An apparatus and a method are provided for automatically collecting a sample of cow's breath. The apparatus comprises an inlet (5) in an animal stall, e.g. a cattle stall, which is connected to collecting or analysing apparatus. A sensor (16) is provided for sensing a flow of breath into the apparatus. A food incentive is automatically dispensed when the sensor is activated, thereby inducing the animal to provide a breath sample. A method for training an animal to use the apparatus is also described, comprising the distribution of food incentives in the locality of the apparatus at random time intervals, together with the gradual increasing of the length and/or strength of exhalation necessary to result in the dispensing of food incentive.

23 Claims, 4 Drawing Sheets

APPARATUS FOR ANIMAL HEALTH MONITORING

This application is a continuation of PCT/GB98/02302 filed Aug. 3, 1998.

BACKGROUND OF THE INVENTION

1. Field of the Invention

This invention is concerned with apparatus for collection of animal exhalation and extends to feed stalls and milking apparatus including such apparatus.

2. Description of the Related Art

In the field of animal husbandry there is a continuing requirement to improve the overall yields obtained from livestock. Examples of areas in which improved yields are considered to be desirable include milk and meat production. It is generally accepted that the best way of achieving production targets set is to ensure that the animals are in good health. For example, the health of a ruminant animal such as a cow is influenced by its metabolic state. Animals with metabolic deficiencies tend to give yields that are significantly lower than animals which are in good health. Examples of metabolic conditions which adversely affect yield include ketosis and mastitis in cows.

It has become good practice to monitor the health of individual animals in the herd so that any problems arising which may adversely affect yield can be detected and rectified at an early stage. Monitoring techniques employed include weighing and measuring the animals and collecting samples of blood, urine, saliva and semen. By using these techniques a skilled person is able to establish a health profile for each animal.

Although weighing and measuring an animal is non-intrusive, the collection of urine and particularly blood samples is intrinsically intrusive and requires significant manual effort. A requirement to have the samples collected and analysed remotely together with the inevitable delay before receipt of the results and therefore diagnosis represents a significant disadvantage as any adverse condition of the animal may have deteriorated unnecessarily. The collection of blood and urine samples is, therefore, generally inconvenient and is only considered to be feasible on an intermittent rather than a regular basis and thus it is not possible to monitor the animal on a day to day basis using these techniques.

Methods for monitoring animal derived exhalations, particularly their exhaled breath, provide non-intrusive techniques which give useful information about health status. Preferably exhalation derived from the lungs is collected and especially the end tidal portion thereof as this contains components, some of them volatile, which have passed from the blood vessels into the alveoli. It can therefore be appreciated that it is possible by monitoring exhalation derived from the lungs to estimate certain volatile components of blood.

Apparatus and methods for the collection of non-human animal derived exhalation are disclosed in WO 94/12019 and WO 94/12022.

Apparatus for the collection and monitoring of human exhalation samples are well known and have been described in U.S. Pat. No. 4,202,352 and EP 0 650 051. U.S. Pat. No. 4,202,352 discloses apparatus which provide a solution to the problem of how to collect a series of rapid and shallow breaths from an infant. EP 0 650 051 discloses apparatus for the collection of human exhalation which includes a mouthpiece into which a patient is required to exhale deeply in response to instructions given by an operator. In both U.S. Pat. No. 4,202,352 and EP 0 650 051 the patients can be considered to be compliant. By compliant it is to be understood that the patient is cooperative. Adult humans in particular are able to understand any instructions given and/or are not disturbed by the presence of the collection apparatus, while infants do not offer serious resistance. Collection of an exhalation sample from a non-human animal is prone to difficulties. A non-human animal can be considered to be a non-compliant patient; it is unable to follow instructions given to it regarding when and how to provide an exhalation sample and it is easily disturbed by a change in its surroundings. The problem of collecting exhalation from a non-human animal has been addressed in part by WO 97/00444 which provides apparatus suitable for the collection of non-human animal exhalation. The apparatus includes a flow sensor positioned at the inlet which detects the presence of animal exhalation and thereby controls when an exhalation sample is collected. A long, thin inlet tube adapted to be placed in the nostril of the animal for collection of the sample minimises any disturbance experienced.

However, before the apparatus according to WO 97/00444 is used to collect a sample, it is necessary to restrain the animal. This requires considerable manual effort and tends to disturb the animal whose breathing becomes extremely rapid and shallow as a result so that any exhalation sample collected is rendered less representative of blood content.

Collection of a sample using the apparatus of WO 97/00444 requires knowledge regarding the position of the animal's head. The problems associated with the collection of a sample using this apparatus mean that it is not possible to use it in an automated setting without modification. In addition use of the apparatus requires significant manual input which makes its use on a daily or routine basis expensive and time consuming.

There is a need to be able to collect animal exhalation samples, automatically on a routine basis, e.g. daily. There is also a need to be able to collect exhalations closely corresponding in volatiles content to blood, e.g. such as those obtainable from an animal taking deep and regular breaths such as from a relaxed animal. Obtaining such exhalations is required without the uncertainty of whether or not the animals' head is in the correct position for sampling. The present invention addresses these needs.

BRIEF SUMMARY OF THE INVENTION

It is an object of the present invention to provide apparatus for collection of a sample of animal exhalation which is of sufficient quality to be used in a method for monitoring the general health of an animal.

It is a further object of the present invention to provide a method and apparatus for collection of a sample of animal exhalation without the animal being aware of the occurrence of that collection and/or without disturbing it.

It is a still further object of the invention to provide a method and apparatus for collection of animal exhalation on a routine e.g. daily basis thereby to provide an indication of the health of an animal.

It is a further object of the invention to provide a method for training an animal to provide a breath sample using automatic collection apparatus.

A first aspect of the present invention provides apparatus comprising an inlet in flow communication with means for collecting, conditioning and/or analyzing an exhalation sample from an animal, characterised by automatic means for providing an incentive for the animal on detection by sensing means of the receipt in the apparatus of a suitable breath sample, or of action by the animal likely to lead to the collection of a suitable breath sample.

Also according to the first aspect of the invention, a method is provided for monitoring an animal's breath comprising:

(a) providing breath collecting, conditioning and/or analyzing means in flow communication with an inlet;

(b) automatically causing the dispensation of incentives for the animal on detection of the receipt in the apparatus of a suitable breath sample or of action by the animal likely to lead to a collection of a suitable breath sample.

A second aspect of the present invention provides apparatus comprising receiving means adapted to receive a muzzle of an animal, the receiving means including outlet means in flow communication with a means for collecting, conditioning and/or analyzing an exhalation sample, characterised that, in use, insertion of the animal muzzle into said receiving means positions the nostrils of the animal such that exhalation therefrom is directed toward the outlet means.

By using the method and/or apparatus of the present invention, it is possible to collect a good quality sample for analysis automatically without the requirement to manually restrain the animal. Analysis of the sample collected can be used to provide useful information about the health of the animal which, together with other monitoring techniques can be used to establish a health profile for individual animals.

The ability to monitor the health of the animal automatically, i.e. in automated fashion on a daily basis provides many advantages. It is possible to detect any deterioration in the health of an animal at an early stage and rectify any deficiency before the condition becomes too serious. In this way it is possible to optimise animal product yields obtained.

It has been established by Kilger, Foster, Temple, Matthews and Bremner; Applied Animal Behaviour Science, 30 (1991) 141–166 and by Moore, Whittlestone, Mullord, Priest, Kilgour and Albright; Journal of Dairy Science, 58 (1975) 1531–1535 that an animal such as a cow can be trained, i.e. conditioned to perform certain tasks if, upon successful completion of those tasks, the animal is rewarded with, for example, food. The complexity of the task may vary from inserting its muzzle in the receiving means for a predetermined period of time to pressing a button within or adjacent the receiving means one or more times. Ideally the task will be the delivery of a satisfactory sample of exhalation reflecting blood volatiles content to the inlet means. By conditioning the animal in this way it is possible to collect a sample of animal exhalation automatically in reliable fashion.

In a third aspect of the invention, a method is provided for training an animal to use automatic breath sample apparatus, the method comprising training the animal to exhale with sufficient flow rate and/or for a sufficient duration to operate the apparatus, with its head in a particular position, using one or more of the following steps:

(a) providing incentives at regular or random time intervals in the locality of an inlet to the apparatus;

(b) decreasing the intervals of time between, or ceasing, the provision of any regular or random incentives as the animal's performance improves;

(c) detecting the flow rate and/or duration of any exhalations by the animal into the apparatus and initially providing an incentive when an exhalation is detected which is not of sufficient duration and/or flow rate to operate the apparatus;

(d) decreasing the flow rate and/or duration of exhalation required to cause the provision of any incentives based on an insufficient flow rate and/or duration of exhalation, as the animal's performance improves.

The apparatus conveniently includes a mounting which is adapted to be attached to a feeder station, e.g. a standard forward feeder station. It is preferably of form and size so that in use there are no superfluous recesses between the sides of the mounting and the feeder into which the animal can place any part of its head. It is also preferred that the apparatus does not limit access of the animal to the trough into which feed is dispensed. Preferably the apparatus is positioned above the trough in use. It is especially preferred that the width of the mounting corresponds to that of the animal feeder station and that the animal is not hindered in its access to the food trough.

The apparatus and its mounting are preferably smooth and free of any projections that would otherwise encourage the animal to chew it.

The apparatus is preferably formed of materials sufficiently robust to withstand impact with any part of with the animal. The materials are also preferably resistant to any erosion caused by the animal licking or rubbing any part of the mounting. Suitable mounting materials include fibre glass, polycarbonates and impact resistant plastics. By impact resistant it is to be understood that the material is able to withstand impact with the body and particularly the muzzle of an animal.

The receiving means is preferably a recess in a housing adapted to receive the muzzle of an animal but may include other structures adapted to capture animal exhalation through the provision of a structured airflow. It is preferred that the receiving means are of a size and shape which correspond to the size and shape of the animal muzzle. It is also preferred that the receiving means provides for easy insertion and removal of the animal muzzle. In a preferred embodiment of the apparatus, the receiving means is shaped to provide for limited movement of the animal muzzle once inserted. By limited movement it is to be understood that movement of the animal muzzle within the cross-sectional area of the receiving means is limited but easy insertion and removal of the animal muzzle therefrom is allowed.

The outlet means preferably comprises openings included in the receiving means which are preferably sized to correspond to the cross-sectional area of the exhalation of the animal. It is preferred that the openings are positioned to be in alignment with the nostrils of the animal upon insertion of the animal muzzle. It is especially preferred that the apparatus includes two openings, one for each nostril.

Means of communication is preferably provided by a flow path between the openings and the collection, conditioning and/or analyzing means. A single flow path from the openings may be provided. Alternatively more than one flow path may be provided, the number of paths corresponding to the number of openings in the receiving means. It may be preferable if more than one flow path is provided, to direct the exhalation from one path along a route which bypasses the collection, conditioning and/or analyzing means.

Suitable collection means include apparatus as described in WO 97/00444 for the collection and temporary storage of the sample prior to analysis. Alternatively apparatus adapted for on-line sampling of exhalation may be preferred. The invention therefore also provides apparatus which includes means for the collection of an animal exhalation sample.

It may be desirable to include flow sensing means within one or more of the aforementioned flow paths to detect the presence of animal exhalation. Preferably the flow sensing means are positioned adjacent the openings. It is especially preferred that the flow sensing means are positioned within the flow path that bypasses the inlet of the collection means.

Means for conditioning the sample will be well known to person skilled in the art and include means for monitoring and/or controlling one or more of the temperature, pressure, humidity, velocity and/or extent of dilution of the sample. The invention also provides apparatus which includes means for conditioning the exhalation sample collected.

Means for analyzing the sample will also be known to a skilled person and may be included with the apparatus of the present invention. Typically the analysis means include for example gas chromatography, mass spectrometry, infra red and ultra violet spectrometry, electrochemical sensors and sensors for detecting antigens, viruses and bacteria. Some of these means of analysis may be sensitive to the condition of the sample, for example the humidity, and it may be necessary to condition the sample accordingly beforehand, e.g. electrochemical sensors benefit from humidity control.

It will be appreciated that the size and shape of the receiving means will not necessarily be suitable for the muzzle of every animal. As young animals tend to have smaller muzzles their movement within the recess is not as limited. This greater range of movement may mean that any exhalation of the animal is lost to the surroundings. To overcome any disadvantages associated with unwanted loss of exhalation the apparatus may be provided with sealing means which prevent unwanted loss of exhalation during the period in which the animals muzzles is inserted into the recess.

Sealing means may for example comprise an apertured resilient sheet placed in front of the receiving means in use thereby forming a seal with the animal's head or muzzle. Alternatively the resilient sheet may comprise an aperture having one or more incisions cut into it to allow various sized muzzles to pass through the aperture. When not in use the aperture is of smaller cross-sectional area than that of the receiving means. In use the animal approaches the apparatus and pushes its muzzle through the apertured resilient sheet into the receiving means. As a result the cut portions of the aperture contact the head of the animal thereby forming a seal and the size of the aperture increases by an amount corresponding to the size of the animal's head or muzzle.

In this way it is possible to collect a sample of animal exhalation regardless of the size of the head or muzzle. The invention further provides apparatus which include sealing means as hereinbefore described.

In use the trained or otherwise conditioned animal approaches the feed station and places its muzzle in the receiving means for a predetermined period before a food reward is deposited into the feed trough. Upon insertion of its muzzle into the receiving means the nostrils of the animal align with the openings therein. During the period of time in which the animal's muzzle is in position, the animal is relatively relaxed and breathes deeply. As the animal exhales, the exhalation passes from its nostrils, through the openings and is directed along the flow path for subsequent collection, conditioning and/or analysis, preferably under influence, e.g. flow produced by a vacuum.

It will therefore be appreciated that the use of the apparatus of the invention greatly facilitates the collection of a sample of animal exhalation. As there is no need to catch and restrain the animal, it is relaxed and breathing deeply when a sample is collected. The animal approaches stall of its own accord. The sample collected using the apparatus of the invention is consistently of good quality. The high quality of the samples collected can also be attributed to the ability to correctly position the animal's head, and consequently its nostrils for sample collection, and its relaxed condition. This facilitates the selective collection of non-rumen derived exhalation as access of the animal's mouth to the openings is substantially prevented. In essence, the apparatus provides for collection of a sample without the animal being aware that a sample is being taken.

The apparatus may be provided with actuation means which either initiate the collection, conditioning and/or analysis of a sample or turn the apparatus to a "stand by" mode, the collection, conditioning and/or analysis of the exhalation sample being subsequently initiated by the detection by the sensing means of the presence of animal exhalation.

Actuation means may include means for recognising the presence of an animal at the feed station. Each animal may, for example, be provided with a transponder which generates a recognition signal in response to an initiation signal generated by corresponding circuitry at or in the vicinity of the feed station. The recognition signal can be used to detect the presence of and/or identify the animal approaching the station. The signal may also be used to initiate a delay period before food is dispensed into the feed trough. Preferably detection of the recognition signal is used to turn the apparatus to "stand by"; switching the apparatus from "stand by" to "collection" is initiated upon detection by the sensing means of the presence of animal exhalation. It is especially preferred that feed is not dispensed unless exhalation is detected.

Alternatively, in a preferred embodiment of the invention the apparatus is provided with actuation means in the form of a switch. The switch is preferably positioned within the receiving means and is turned from "off" to "on" by contact with the animal muzzle when it is placed within the receiving means. The switch is preferably a push switch which is operated by the pressure applied thereto by said animal. Suitable forms of switches will be apparent to a person skilled in the art. Hydraulically operated switches are especially preferred.

It is preferred to position the switch below the openings when in use. It is especially preferred to position the switch so that when in use the nostrils of the cow are aligned with the openings of the recess. It is believed that the use of the switch provides for more accurate and reliable positioning of the nostrils for collection of an animal exhalation sample. It is also believed that by positioning the switch below the openings when in use, it possible to substantially reduce or eliminate emanations from the rumen since any exhalation from the mouth is deflected by the switching means away from the openings. The switch may therefore take the form of a deflector which deflects any rumen derived gas which may be emitted away from the openings. The provision of a switch facilitates the selective collection of non-rumen derived exhalation.

Collection of an exhalation sample requires the animal to approach the feed station, place its muzzle within the receiving means and depress the switch. As mentioned previously the animal may be trained to operate the switch either one or several times and/or for a predetermined period before food is dispensed. During the period in which the switch is depressed the animals head is positioned so as to allow the collection of a good quality exhalation sample. The animal is also breathing deeply which means that it is possible to collect, if desired, end tidal exhalation rather than dead space exhalation associated with short shallow breaths.

Upon depression of the switch by the animal the collecting apparatus may be switched from "off" to "on" or "standby". Switching the apparatus "on" provides for the collection of a sample irrespective of its nature. If the apparatus is switched to "standby", a sample is only collected upon subsequent detection by the lung exhalation sensing means of the presence of animal exhalation. The sensing means may be calibrated to only switch the apparatus on once a certain threshold level of exhalation has been achieved. In this way it is possible to ensure that only exhalation comprising deep breaths are collected. The lung exhalation sensing means may be flow sensing means as in WO 9700444.

A particularly preferred embodiment of the invention provides apparatus having both switching and recognition means. This makes it is possible to monitor individual animals as they arrive at the animal feeder station on a regular basis.

A particularly useful application for the apparatus and/or method of the invention is in the detection and monitoring of methane and dimethyl sulphide in animal's breath. Accordingly a preferred embodiment of the invention includes means for analyzing breath for quantitative or qualitative detection of methane and/or dimethyl sulphide.

The present invention is particularly suitable for mounting on a standard forward feeder station and a second aspect of the invention provides an animal feeder station which includes apparatus comprising mounting means as herein before described.

Alternatively, the apparatus may included in a milking system. In this case the trained animals are required to perform the tasks as herein before described before issuance of a food reward and optionally this occurs before admission to the milking stall. A third aspect of the present invention provides a milking system which includes apparatus as herein before described.

The present invention also provides a method for taking an exhalation sample from an animal comprising conditioning the animal to place its muzzle in an apparatus as herein before described and exhale and collecting an exhalation sample.

Many other preferred features of the invention are set out in the dependent claims hereto and the advantages of these and other features of the invention will be apparent from the following description.

BRIEF DESCRIPTION OF THE DRAWINGS

Two embodiments of the invention will now be described by reference to the following figures and examples. These figures and examples are provided for the purpose of illustration only and are not intended to limit the scope of the claimed invention. Variations on these figures and examples falling within the scope of the claims will be apparent to a person skilled in the art.

DETAILED DESCRIPTION OF THE INVENTION

Figure 1:
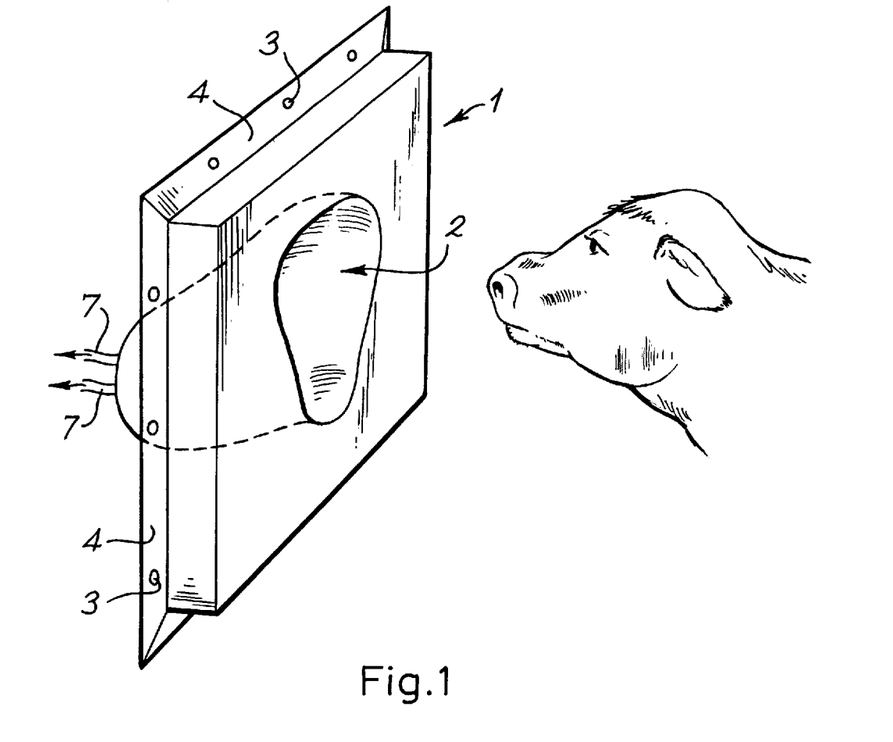
FIG. 1 is a representation of part of the first embodiment of the invention.
Figure 2:
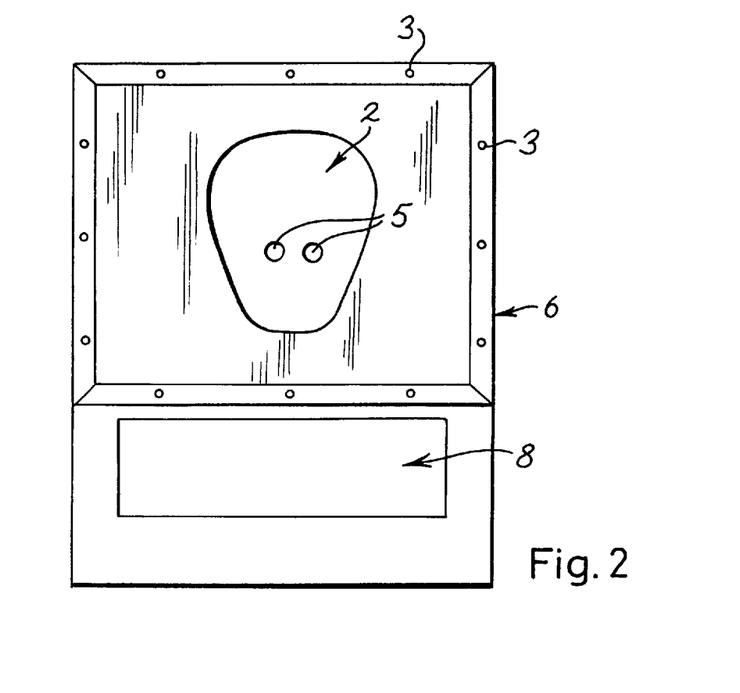
FIGS. 2 and 3 show cross sections through parts of the first embodiment and a modification thereof, mounted on an animal feeder station.

FIG. 1 shows apparatus comprising a mounting 1 having receiving means 2 in the form of a recess adapted to receive the muzzle of an animal. The receiving means is moulded to the shape of the animal's muzzle and is preferably tapered for ease of muzzle insertion and removal. Fixing means 3 adjacent the edges of the mounting 4 are used to attach the apparatus to the animal feed station 6 (FIG. 2). Exhalation from the animal passes from its nostrils through the openings 5 and into one or more flow paths 7 provided for the transfer of the sample from the apparatus to any of the collection, conditioning and/or analyzing means that may be present.

Figure 3:
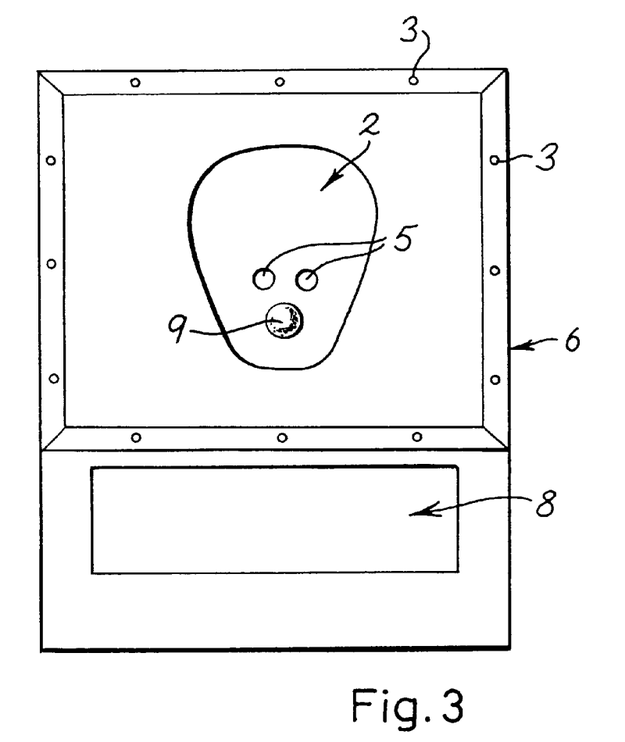

FIGS. 2 and 3 show the apparatus mounted in a standard forward feeder station 6. The apparatus is sized so that the side and top edges of the apparatus 4 are positioned adjacent the side and top edges of the feeder station. By occupying most of the upper area of the feeder station, the animal is only able to insert its muzzle into the receiving means 2 since any recesses at the sides where the mounting is attached to the feeder station are far too small for the animal's muzzle. The trough 8 into which feed is dispensed is positioned below the mounted apparatus in use.

In FIG. 2, the receiving means comprises a recess including two openings 5 with which the animal's nostrils become aligned upon insertion by the animal of its muzzle in use. The area occupied by the openings preferably corresponds to the area occupied by the exhalation path of the animal. It is especially preferred that the openings correspond to the size of the animal's nostrils.

In FIG. 3, the receiving means further comprises a switch 9 in the form of a button which is switched from the "off" to the "on" state when depressed as a result of insertion by the animal of its muzzle. The switch 9 is preferably positioned below the openings 5 in use. It is especially preferred that the position of the switch corresponds to the position occupied by the animal's mouth when inserted into the recess. The switch 9 can then function to prevent or discourage the animal from exhaling through its mouth and/or deflecting any exhalation from the mouth away from the openings 5. In this way it is possible to selectively collect non-rumen derived exhalation without needing to know the position of the animal's mouth.

In use the trained animal approaches the feeder 6 and inserts its muzzle into the receiving means 2 with the expectation that it will receive, in due course, a food reward. The feeding station 6 may be provided with electronic circuitry that responds to signals emitted by a transponder attached to the animal (response means). As the animal approaches the feeder station, the response means receives a signal from the transponder. Upon receipt of this signal the apparatus are turned from "off" to "standby". The animal places its muzzle in the receiving means 2, and thus aligns its nostrils with the openings 5 and exhales. Exhalation from the animal passes over means which detects the presence of animal exhalation, e.g. a flow sensor. Upon the detection of the presence of animal exhalation, the flow sensor generates a signal. The flow sensor may be calibrated to only generate a signal when the flow of exhalation reaches a certain threshold level. The signal generated by the flow sensor is then used to turn the apparatus "on" thereby initiating the collection, conditioning and/or analysis of exhalation.

Alternatively, upon approach by the animal to the feeder station and receipt by the response means of the signal from the transponder the apparatus may be turned from "off" to "on" so that collection, conditioning and/or analysis of animal exhalation may be effected as the animal places its muzzle within the receiving means.

In addition to or instead of the use of transponder and response means the provision in FIG. 3 of a switch 9 may be used to similar effect. The animal inserts its muzzle into the receiving means 2, aligns its nostrils with the openings 5 and depresses the switch 9 thereby generating a signal that turns the apparatus from "off" to "standby". As the animal exhales, its exhalation passes over a sensor which detects the presence of animal exhalation, preferably a flow sensor. Upon the detection of the presence of animal exhalation, this flow sensor generates a signal. The sensor may be calibrated to only generate a signal when the flow of exhalation reaches a certain threshold level. The signal generated by the sensor is then used to turn the apparatus "on" thereby facilitating the collection, conditioning and/or analysis of exhalation.

In the alternative, depression of the switch 9 by the animal may generate a signal which turns the apparatus from "off" to "on" thereby facilitating the collection, conditioning and/or analysis of the exhalation sample.

Figure 4:
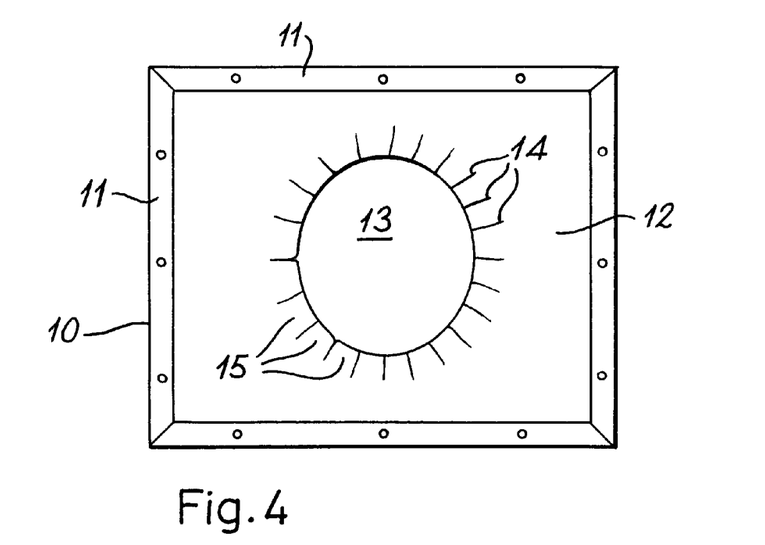
FIG. 4 shows sealing means adapted to be used with the first embodiment.

FIG. 4 shows aperture sealing means 10 which can be placed adjacent the mounting 1. The sealing means are of a size so that when in use the upper and side edges 11 of the sealing means 10 are positioned adjacent the upper and side edges of the animal feeder station 6. The area of the sealing means corresponds to that of the mounting 1 and in use the sealing means 10 are placed on the front of the mounting means 1. The sealing means 10 comprise a resilient sheet 12 having an aperture 13. The aperture 13 is of smaller cross-sectional area than that of the receiving means and may further comprise a plurality of incisions 14 extending radially from the edge of the aperture 12 towards the edges 11 of the sealing means 10. The plurality of incisions together form a "fringe" having a plurality of elements 15 around the edge of the aperture.

In use, the animal approaches the apparatus and pushes its muzzle through the aperture 13 prior to inserting its muzzle in the receiving means 2. As it pushes its muzzle through the aperture 13, the elements 15 of the fringe are forced against the muzzle of the animal thereby forming a seal between the muzzle of the animal and the apparatus together with a concomitant increase in the size of the aperture 13.

Figure 5:
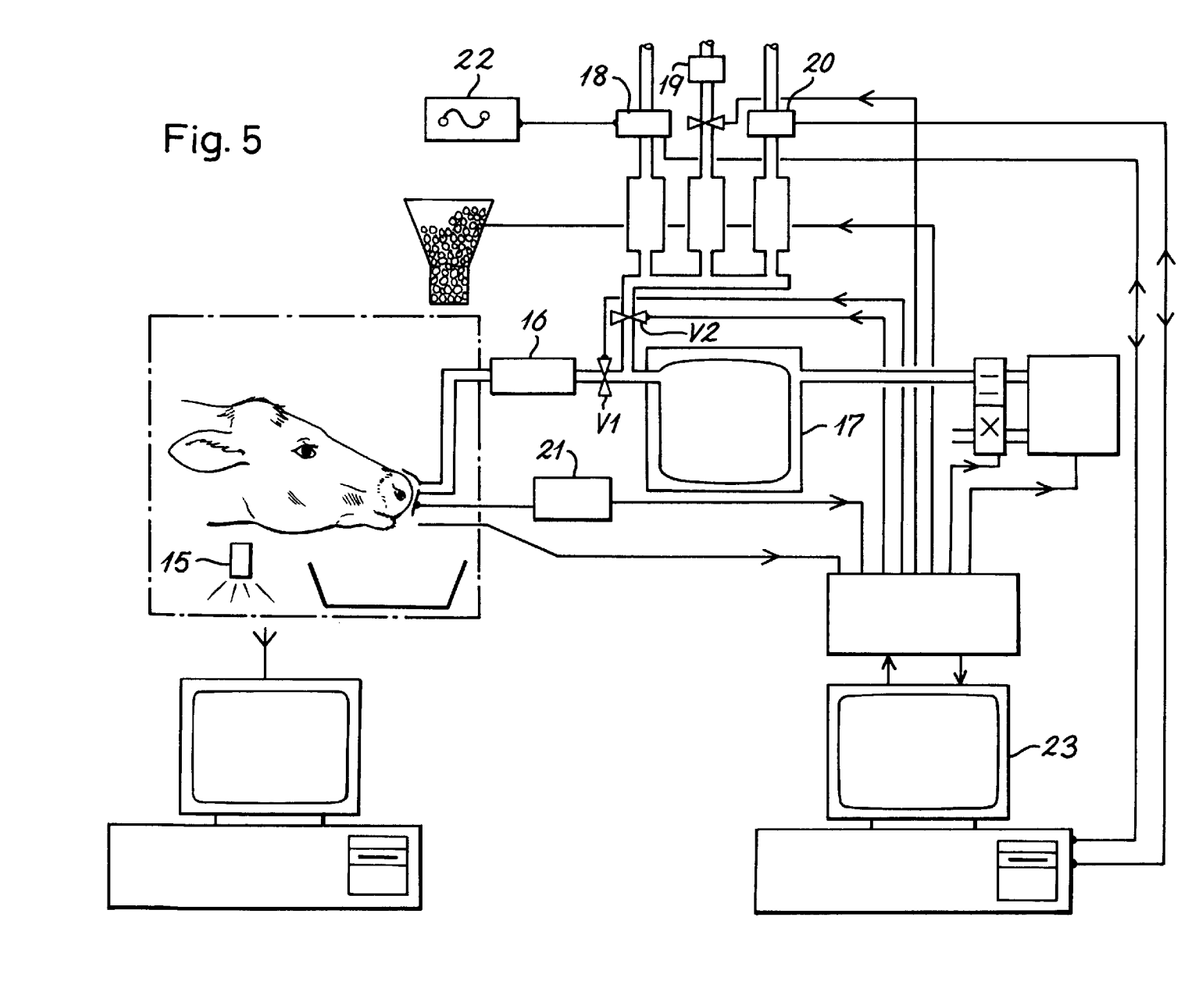
FIG. 5 is a diagrammatic representation of the first embodiment.

In FIG. 5, the apparatus forms part of a system used for the collection, conditioning and/or analysis of animal exhalation samples. As the animal approaches the apparatus 1 a transponder 16 attached to the animal causes a signal to be generated by the response means 17 thereby turning the apparatus to "stand by" from "off". The animal inserts its muzzle into the receiving means 2 of the apparatus 1, aligns its nostrils with the openings 5, depresses the switch 9 and exhales. Exhalation passes from the animal's nostrils through the openings 5. The path followed by the exhalation is then split. Most of the exhalation is passed from the openings through a filter 16 and into collection means 19 where it is stored prior to conditioning and/or analysis. Conditioning may take place in the collection means 19 prior to analysis by analyzing means 20, 21 and 22. A small proportion of the exhalation is diverted over flow sensing means 23 which generates a signal upon detecting the presence of exhalation. The flow sensing means may be calibrated to generate a signal only when the flow of exhalation exceeds a predetermined threshold limit. The signal generated by the flow sensing means turns the apparatus from "standby" to "on" so that exhalation is passed from the openings 5 to the collection means 19 and on to analyzing means 20, 21 and 22. The system is controlled by signal processing and power control means 24. The signal generated by the analyzing means can be displayed on a screen 25 and provides an indication of the condition of the animal. The output from the system can therefore be used in a method for establishing a health profile for an animal.

Figure 6:
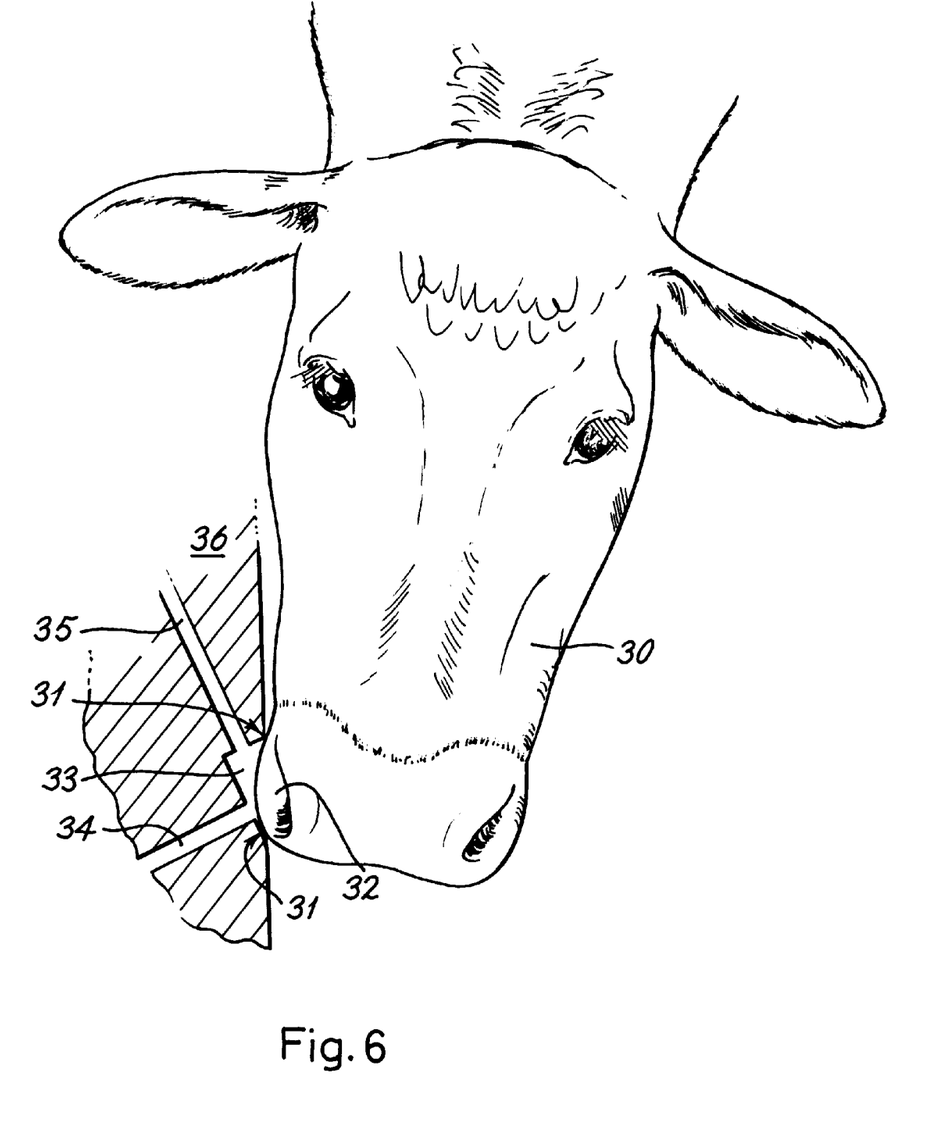
FIG. 6 is a representation of an inlet part of the second embodiment of the invention.

A second embodiment of the invention is shown in part in FIG. 6. In this embodiment, a simple orifice 33 is provided in the side wall 35 of a cattle feeding stall. The orifice 33 has two channels 34, 35 leading from it, the first channel 34 leading to a flow sensor and a second channel 35 leading to a collecting bag and, from the bag to an analysis device.

In use, a cow, whose head is represented as numeral 30 in FIG. 6, presses one nostril 32 against the orifice 33 thereby providing a breath sample.

Apart from the different arrangement of the orifice, this embodiment functions in essentially the same way as the previous embodiment, that is to say the animal will be rewarded with feed on exhaling a sample of sufficient volume into the orifice, this being detected by the flow sensor in the passage 34.

The use of an orifice on the side of a stall means that the cow cannot easily apply her mouth to the orifice and, even if she does, it is difficult to make an effective seal around the orifice so that flow sufficient to generate a reward is produced. In contrast, a nostril can be easily applied and the soft tissue around a cow's nostril forms an excellent seal around the orifice indicated at 31 in FIG. 6.

Apart from the arrangement of the orifice/inlet, all the features of the first embodiment, including its variations, are applicable to the second embodiment.

It has been found that cows can be trained "automatically" to use the apparatus of either of the embodiments as follows. Cows are identified automatically by means described above and this information is communicated to the automatic control system for the breath detection apparatus. A "new" cow can there be identified and training regime initiated by the control system.

The first aspect of "training" is to distribute small quantities of food at random (or possibly regular) time intervals in the stall to encourage the cow to enter and investigate. Additionally, a substance which the cow likes to lick may be released in or adjacent the inlet/orifice to encourage her to put her head in the appropriate position. At this stage, the cow may be restrained by some means which comes into action automatically.

The second aspect of the training is to reduce the sensitivity threshold of the flow sensor so that the smallest flow rate/volume will cause feed to be released. Once the cow "learns" that putting her nostril next to the aperture or putting her muzzle in the recess (depending on which embodiment is being used) results in feed, i.e. once the release of feed is being triggered fairly regularly, the threshold can be raised so that a higher volume of breath must be exhaled or a higher flow rate achieved before food will be dispensed. At this stage the regular or random dispensation of feed unconnected with the detection of flow of breath may however be stopped or the time interval between portions of feed being dispensed may be increased.

Again, once the cow has learnt to trigger feed regularly, the threshold can be increased, and this can be continued until the desired threshold of flow rate and/or volume is regularly achieved. At this point, if it has not already been done, the random/regular distribution of feed would normally be halted.

In practice it has been found that a good way of retaining the cow's interest is to provide the food incentive after an exhalation of perhaps a tenth of the volume which needs to be collected for analysis. Approximately 2 litres needs to be collected for analysis normally, so a reward could be provided for an exhalation of perhaps 200 ml. It has been found that if a cow is set too big a task, it will not correctly operate the apparatus and will leave the stall (if not restrained).

It has also been found that the activation of the flow sensor, which is associated with a noise, gives an indication to a cow that she is performing the task for which feed will be provided and this can become an incentive in its own right. Of course this sort of effect could be achieved in many other ways if the flow sensor did not make a noise, e.g. a visual olfactory or an alternative auditory indication could be given.

What is claimed is:

1. An apparatus comprising an inlet (5) in flow communication with means (18, 19, 20) for collecting, conditioning and/or analyzing an exhalation sample from an animal, characterized by automatic means for providing an incentive for the animal on detection by a sensing means (16) of the receipt in the apparatus of a suitable breath sample, or of an action by the animal likely to lead to the collection of a suitable breath sample.

2. Apparatus as claimed in claim 1, wherein the said sensing means (16) is arranged to detect one or more of the following:
   (a) a flow of breath in the apparatus;
   (b) the location of the animals head in a given position;
   (c) the operation by the animal of a switch (9).

3. Apparatus as claimed in claim 1, comprising means for providing to the animal auditory or other indicia as a precursor to providing an incentive.

4. Apparatus as claimed in claim 2, wherein the said sensing means (16) is arranged to detect certain characteristics of a flow of breath in the apparatus and to provide an incentive only if the detected characteristics meet given criteria.

5. Apparatus as claimed in claim 2, wherein two flow paths lead from the inlet, one leading to means for detecting a flow of breath and the other leading to the said collecting, conditioning and/or analyzing means.

6. Apparatus as claimed in claim 1, wherein the inlet (5) is located in receiving means (2) adapted to receive the animal's muzzle, the receiving means being arranged such that insertion of the animal's muzzle into the receiving means positions a nostril of the animal such that exhalation therefrom is directed towards the inlet.

7. Apparatus as claimed in claim 1, comprising an animal stall in one side wall (36) of which is located an orifice (33) in communication with the said inlet, so arranged as to enable an animals' nostril (32) to effect a substantial seal around the orifice (33) when pressed against it.

8. Apparatus according to claim 1 in which the openings of the inlet means are aligned with the nostrils of the animal upon insertion of the animal muzzle into the recess.

9. Apparatus according to claim 1 which further comprises one or more means for detecting the presence of, collecting, conditioning and/or analyzing animal exhalation.

10. Apparatus according to claim 1 which further comprises actuation means.

11. Apparatus according to claim 10, in which the actuation means comprise means for recognising the animal.

12. Apparatus according to claim 10, in which the actuation means comprise a switch positioned (9) within the receiving means.

13. A method of monitoring an animal's breath comprising:
   (a) providing breath collecting, conditioning and/or analyzing means in flow communication with an inlet:
   (b) automatically causing the dispensation of incentives for the animal on detection of the receipt in the apparatus of a suitable breath sample or of an action by the animal likely to lead to the collection of a suitable breath sample.

14. A method as claimed in claim 13, wherein the dispensation of incentives is automatically caused on detection of one or more of the following:
   (a) a flow of breath in the apparatus;
   (b) the location of the animals head in a given position;
   (c) the operation by the animal of a switch (a).

15. A method as claimed in claim 13, comprising providing to the animal auditory or other indicia as a precursor to providing an incentive.

16. A method as claimed as claimed in claim 14, comprising detecting certain characteristics of a flow of breath in the apparatus and providing an incentive only if the detected characteristics meet given criteria.

17. An Apparatus comprising receiving means (2) adapted to receive a muzzle of an animal, the receiving means including inlet means (5) in flow communication with a means for collecting, conditioning and/or analyzing an exhalation sample, characterized that in use, insertion of the animal's muzzle into said receiving means positions the nostrils of the animal such that exhalation therefrom is directed toward the inlet means.

18. Apparatus according to claim 17, in which the receiving means is further characterized by means for limiting the movement of the animal muzzle within the recess.

19. Apparatus according to claim 17, in which the inlet means comprises two openings.

20. An animal feed stall which includes apparatus according to claim 17.

21. An animal milking system which includes apparatus according to claim 17.

22. A method for taking an exhalation sample from an animal comprising conditioning the animal to place its muzzle in an apparatus as claimed in claim 17.

23. A method of training an animal to use automatic breathing sampling apparatus comprising training the animal to exhale with sufficient flow rate and/or for a sufficient duration to operate the apparatus with its head in a particular position, using one or more of the following:
   (a) providing incentives at regular or random time intervals in the locality of a inlet to the apparatus;
   (b) decreasing the intervals of time between, or ceasing, the provision of any regular or random incentives as the animals' performance improves;
   (c) detecting the flow rate and/or duration of any exhalations by the animal into the apparatus and initially providing an incentive when an exhalation is detected which is not of sufficient duration and/or flow rate to operate the apparatus;
   (d) gradually increasing the flow rate and/or duration of exhalation required to cause the provision of any incentives based on an insufficient flow rate and/or duration of exhalation.

* * * * *